US012036267B2

(12) United States Patent
Rapacioli et al.

(10) Patent No.: US 12,036,267 B2
(45) Date of Patent: Jul. 16, 2024

(54) LACTOFERRICIN AND LACTOFERRAMPIN FOR TREATING INFECTIONS

(71) Applicant: BICT S.R.L., Lodi (IT)

(72) Inventors: Silvia Rapacioli, Lodi (IT); Roberto Verga, Lodi (IT); Emma Mazzei, Lodi (IT); Stefano Zucchinali, Lodi (IT)

(73) Assignee: BICT S.R.L., Lodi (IT)

( * ) Notice: Subject to any disclaimer, the term of this patent is extended or adjusted under 35 U.S.C. 154(b) by 0 days.

(21) Appl. No.: 16/633,194

(22) PCT Filed: Jul. 24, 2018

(86) PCT No.: PCT/IB2018/055496
§ 371 (c)(1),
(2) Date: Jan. 23, 2020

(87) PCT Pub. No.: WO2019/021175
PCT Pub. Date: Jan. 31, 2019

(65) Prior Publication Data

US 2021/0154273 A1 May 27, 2021

(30) Foreign Application Priority Data

Jul. 26, 2017 (IT) ........................ 102017000085409

(51) Int. Cl.

| | |
|---|---|
| ***A61K 36/00*** | (2006.01) |
| ***A23K 10/30*** | (2016.01) |
| ***A23K 20/147*** | (2016.01) |
| ***A23L 33/00*** | (2016.01) |
| ***A23L 33/105*** | (2016.01) |
| ***A23L 33/18*** | (2016.01) |
| ***A61K 36/45*** | (2006.01) |
| ***A61K 36/61*** | (2006.01) |
| ***A61K 36/82*** | (2006.01) |
| ***A61K 38/16*** | (2006.01) |
| ***A61K 38/40*** | (2006.01) |
| ***A61P 31/00*** | (2006.01) |

(52) U.S. Cl.
CPC .............. *A61K 38/40* (2013.01); *A23K 10/30* (2016.05); *A23K 20/147* (2016.05); *A23L 33/105* (2016.08); *A23L 33/18* (2016.08); *A23L 33/40* (2016.08); *A61K 36/45* (2013.01); *A61K 36/61* (2013.01); *A61K 36/82* (2013.01); *A61K 38/164* (2013.01); *A61P 31/00* (2018.01); *A23V 2002/00* (2013.01)

(58) Field of Classification Search
None
See application file for complete search history.

(56) References Cited

U.S. PATENT DOCUMENTS

2009/0270309 A1* 10/2009 Cornish .................. A61P 29/00 514/1.1

OTHER PUBLICATIONS

Maekawa et al. (2002) Biol. Pharm. Bull. 25(1): 118-121. (Year: 2002).*
Plate et al. (2006) Journal of Chromatography A 1117: 81-86. (Year: 2006).*
Tallarida (2011) Genes & Cancer 2(11): 1003-1008. (Year: 2011).*
Flores-Villaseaor H et al., "Lactoferrin and lactoferrin chimera inhibit damage caused by enteropathogenicin HEp-e cells", Biochimie Masson, Paris, FR, vol. 94, No. 9, May 12, 2012, pp. 1935-1942.
Search Report and Written Opinion of PCT/IB2018/055496 of Nov. 20, 2018.
Xu G et al., "Lactoferrin-derived peptides and lactoferricin chimera inhibit virulence factor production and biofilm formation in Pseudomonas aeruginosa", Journal of Applied Microbiology, Wiley-Blackwell Publishing LTD, GB, vol. 109, No. 4, Jan. 1, 2010, pp. 1311-1318.

* cited by examiner

*Primary Examiner* — Russell G Fiebig
(74) *Attorney, Agent, or Firm* — Silvia Salvadori, P.C.; Silvia Salvadori

(57) ABSTRACT

A composition is disclosed for the treatment of infections caused by pathogenic agents, such as bacteria, fungi, or yeasts. In particular, the composition according to the invention comprises a synergistic association of two peptides, namely lactoferricin and lactoferrampin, which has been shown to be significantly active against such pathogenic agents.

6 Claims, No Drawings

LACTOFERRICIN AND LACTOFERRAMPIN FOR TREATING INFECTIONS

This application is a U.S. national stage of PCT/IB2018/055496 filed on 24 Jul. 2018, which claims priority to and the benefit of Italian Application No. 102017000085409 filed on 26 Jul. 2017, the contents of which are incorporated herein by reference in their entireties.

FIELD OF THE INVENTION

The present invention relates to a composition for the treatment of infections caused by pathogenic agents, such as bacteria, fungi, or yeasts. In particular, the composition according to the invention comprises a synergistic association of two peptides, namely lactoferricin and lactoferrampin, which has been shown to be significantly active against such pathogens.

BACKGROUND ART

Antibiotic resistance is a phenomenon which is now recognised and widespread throughout the world.

The development of drug resistance is a normal evolutionary process. Typically, within a colony of microbes which are sensitive to a certain drug, there are some microbes which are naturally resistant; this phenomenon is known as 'primary insensitivity'. When the antibiotic destroys sensitive bacteria, those which are insensitive to the drug and were—until that moment—in a dormant state, begin to multiply. Or it may happen that resistance develops as a result of mutations in the genetic material of the bacterium, or upon exchange of resistance-conferring genes between bacteria.

Although this phenomenon is natural, it is accelerated and aggravated by incorrect use of antibiotic drugs. One of the main factors contributing to resistance is the practice of treating farm animals with low doses of antibiotics to promote growth and prevent diseases within the overcrowded environments of intensive farms. This practice has been prohibited in Europe since 2006 but about 80% of antibiotics used in the United States today are used on animals.

One of the practices deemed most harmful is the habit of using antibiotics to treat viral infections, when they are in no way useful therefor. Even not following instructions when taking antibiotics, for example at lower doses or for a different time than recommended, is believed to help develop resistance. Another practice that has recently been condemned is the tendency, encountered in many hospitals, to prescribe courses of antibiotics for preventive purposes.

An object of the present invention is therefore to provide an alternative solution to the use of antibiotic drugs, which allows to effectively treat infections caused by bacteria, fungi, or yeast, but without triggering resistance phenomena.

SUMMARY OF THE INVENTION

Said object has been achieved by a composition comprising lactoferricin and lactoferrampin, as stated in claim 1.

In a further aspect, the present invention relates to the use of said composition for the treatment of infections caused by pathogenic agents.

In a still further aspect, the present invention relates to the use of said composition as a prebiotic agent in products for human food or animal feed.

In a still further aspect, the present invention relates to formulations comprising said composition and at least one plant extract.

In a still further aspect, the present invention relates to formulations comprising said composition and at least one other natural antimicrobial peptide.

The characteristics and advantages of the present invention will become apparent from the following detailed description and embodiments provided by way of non-limiting examples.

DETAILED DESCRIPTION OF THE INVENTION

The invention therefore relates to a composition comprising lactoferricin and lactoferrampin, wherein lactoferricin is in a lower amount than lactoferrampin. Lactoferricin is a cationic peptide which can be generated by digestion mediated by lactoferrin pepsin. The complete lactoferricin sequence corresponds to the 17-41 fragment of lactoferrin (FKCRRWQWRM KKLGAPSITCVRRAF; LFB0084). In humans, lactoferricin corresponds to lactoferrin fragment 1-47 but consists of two subunits, i.e. fragments 1-11 and 12-47, connected by a disulphide bridge. Lactoferrampin is a cationic peptide characterised by a highly positive charge and a hydrophobic domain, and therefore an amphipathic character. It comprises residues 268-284 and is located in the N1-domain of lactoferrin, in proximity to lactoferricin. Both lactoferrampin and lactoferricin have amphipathic and cationic characteristics, however they have a different amino acid composition and therefore different structures, and consequently their antimicrobial activities differ considerably.

The term "lower amount than" means that lactoferricin is in a lower molar amount than lactoferrampin. The "mole" is the unit of measurement of an amount of a substance according to the International System (IS). One mole of a chemical substance contains $6.02214076 \times 10^{23}$ constituent particles, which may be atoms, molecules, ions, electrons, or other physical particles.

It has surprisingly been found that, in the compositions wherein lactoferricin is present in a lower amount than the lactoferrampin, a significant antimicrobial synergistic effect is achieved, as will be seen in the examples provided below.

Accordingly, in the composition according to the invention, lactoferricin and lactoferrampin are in a weight ratio of at least 1:1.5.

Most preferably, lactoferricin and lactoferrampin are in a weight ratio no higher than 1:100.

In preferred embodiments, lactoferricin and lactoferrampin are in a weight ratio of 1:2 to 1:50.

In further embodiments, lactoferricin and lactoferrampin are in a weight ratio of 1:1.5 to 1:50, preferably 1:1.5 to 1:20, more preferably 1:1.5 to 1:10.

In certain embodiments, the composition of the invention comprises 0.0005 wt % to 15 wt % of lactoferricin and lactoferrampin, based on the composition weight. Preferably, the composition according to the invention comprises 0.005 wt % to 5 wt % of lactoferricin and lactoferrampin. More preferably, the composition according to the invention comprises 0.01 wt % to 1 wt % of lactoferricin and lactoferrampin.

In particularly preferred embodiments, the composition according to the invention comprises 0.01 wt % to 1 wt % of lactoferricin and 0.02 wt % to 10 wt % of lactoferrampin. Even more preferred are embodiments wherein the composition according to the invention comprises 0.03 wt % to 0.1 wt % of lactoferricin and 1 wt % to 8 wt % of lactoferrampin.

In certain embodiments, lactoferricin and lactoferrampin are obtained by enzymatic hydrolysis of lactoferrin, preferably by using an immobilised enzyme, thereby obtaining, respectively, lactoferrin hydrolysate comprising lactoferricin and lactoferrin hydrolysate comprising lactoferrampin.

Suitable enzymes belong to the class of hydrolases which catalyse the breakage of the peptide bond between two consecutive amino acids of the protein in question, in this case lactoferrin. These enzymes exhibit different selectivity towards the different amino acids present, therefore the complete degradation of the protein in the individual amino acid constituents does not take place but rather the generation of peptide fragments of various lengths depending on the position of the amino acids recognised by the hydrolytic enzyme used. Since the enzyme used for hydrolysis can represent an impurity in the product, the process is preferably based on the immobilisation of said enzyme on inert substrate through covalent bonds; immobilisation enables removal of the biocatalyst, at the end of the reaction, by using physical methods (e.g. filtration) and therefore prevents changes in pH and increases in temperature, which are necessary to inactivate the free enzyme but have a negative impact on the activity of the product.

Preferred enzymes are proteases, in particular endoproteases including, preferably, pepsin, clostripain, proteases type XVII, ASP-N endopeptidases, ARG-C proteinases, glutamyl endopeptidases, proteinases, trypsin, thermolysin, subtilisin, chymotrypsin, and mixtures thereof.

In preferred embodiments, said enzyme is pepsin of pork, clostripain, protease type XVII, ASP-N endoproteases, ARG-C endoproteases, or mixtures thereof.

Preferably, the pH at which enzymatic hydrolysis is carried out is not higher than 3, and more preferably is about 2.

The composition according to the invention may further comprise pharmaceutically acceptable excipients. The term "excipient" refers to a compound or a mixture thereof suitable for use in a formulation for the treatment of infections caused by bacteria, fungi, or yeasts. For example, an excipient for use in a pharmaceutical formulation should not generally cause an adverse response in a patient, nor should it significantly inhibit the efficacy of the composition.

Suitable excipients include acidifiers, acidity regulators, anti-caking agents, antioxidants, bulking agents, resistance agents, gelling agents, coating agents, modified starches, sequestering agents, thickeners, sweeteners, diluents, disaggregating agents, glidants, colorants, binders, lubricants, stabilisers, adsorbents, preservatives, humectants, flavourings, filmogenic agents, emulsifiers, wetting agents, release retardants, and mixtures thereof.

The addition of excipients may be carried out by using methods known in the art. Indeed, the components can, for example, be mixed as such or with one or more excipients, either sealed in soft-gel capsules or in solid form, such as a tablet, mini-tablet, micro-tablet, granule, micro-granule, pellet, multiparticulate, micronised particulate, powder, or in the form of a solution, emulsion, gel, vials, drops or sprays.

The composition according to the invention may be administered via oral, nasal, intra-nasal, sublingual, buccal, intramuscular, intravenous, transdermal, sub-cutaneous, external topical, internal topic, rectal, or ocular route.

In a further aspect, the present invention relates to the use of the composition described above for the treatment of infections caused by pathogenic agents, such as bacteria, fungi, or yeasts.

The term "treatment" refers to the effects of the composition of the invention, which is capable of providing a benefit to patients suffering from an infectious disease, for example, an improvement in the patient's condition or a delay in the progression of the disease. In this document, the term "infection", or its synonym "infectious pathology", means the invasion, colonisation and/or multiplication of a micro-organism within or on another host organism. The term "infection" refers to an infectious disease caused by a pathogenic agent, for example a bacterium, a parasite, a protozoa, a virus, or a fungus, including yeasts.

A pathogenic bacterium may originate from one of the following bacterial species: *Staphylococcus* spp, for example, *Staphylococcus aureus* (e.g. *Staphylococcus aureus* ATCC 25923, or *S. intermedius* ATCC 29663, methicillin-resistant *Staphylococcus aureus, Propionibacterium acnes, Porphyromonas gingivalis, Enterococcus* spp, for example, *Enterococcus faecalis* ATCC 29212; *Pseudomonas* spp, for example *Pseudomonas aeruginosa* ATCC 27853; *Mycobacterium* spp, for example *Mycobacterium tuberculosis; Enterobacter* spp; *Campylobacter* spp; *Salmonella* spp (e.g. *Salmonella enteritidis* ATCC13076); *Streptococcus* spp, for example *Streptococcus* group A or B, *Streptococcus pneumoniae, Helicobacter* spp, for example *Helicobacter pylori; Neisseria* spp, for example *Neisseria* gonorrhoea, *Neisseria meningitidis; Borrelia burgdorferi, Shigella* spp, for example, *Shigella flexneri; Escherichia coli* (ATCC 25922); *Haemophilus* spp, for example, *Haemophilus influenzae; Francisella tularensis, Bacillus* spp, for example *Bacillus anthracis; Clostridium* spp, *Clostridium botulinum, Yersinia* spp, for example, *Yersinia pestis; Treponema* spp; *Burkholderia* spp, for example *Burkholderia cepacia* ATCC 17759, *B. mallei* and *B. pseudomallei; Stenotrophomonas* spp, for example *Steenotrophomonas maltophilia* ATCC 13637.

A fungal pathogen can be derived from one of the following fungal species (including yeasts): *Candida* spp. (for example *C. albicans*), *Epidermophyton* spp. *Exophiala* spp. *Microsporum* spp. *Trichophyton* spp. (for example *T. rubrum* and *T. interdigitale*), *Tinea* spp. *Aspergillus* spp. *Blastomyces* spp. *Blastoschizomyces* spp. *Coccidioides* spp. *Cryptococcus* spp. (for example *Cryptococcus neoformans*), *Histoplasma* spp. *Paracoccidiomyces* spp. *Sporotrix* spp. *Absidia* spp. *Cladophialophora* spp. *Fonsecaea* spp. *Phialophora* spp. *Lacazia* spp. *Arthrographis* spp. *Acremonium* spp. *Actinomadura* spp. *Apophysomyces* spp., *Emmonsia* spp. *Basidiobolus* spp. *Beauveria* spp. *Chrysosporium* spp. *Conidiobolus* spp. *Cunninghamella* spp. *Fusarium* spp. *Geotrichum* spp. *Graphium* spp. *Leptosphaeria* spp. *Malassezia* spp. (*for example, Malassezia furfur*, or *M. pachydermatis* DSM 6172), *Mucor* spp. *Neotestudina* spp. *Nocardia* spp., *Nocardiopsis* spp. *Paecilomyces* spp. *Phoma* spp. *Piedraia* spp. *Pneumocystis* spp. *Pseudallescheria* spp. *Pyrenochaeta* spp. *Rhizomucor* spp. *Rhizopus* spp. *Rhodotorula* spp. *Saccharomyces* spp. *Scedosporium* spp. *Scopulariopsis* spp. *Sporobolomyces* spp. *Syncephalastrum* spp. *Trichoderma* spp. *Trichosporon* spp. *Ulocladium* spp. *Ustilago* spp. *Verticillium* spp. *Wangiella* spp.

Preferably, the treatment is against a pathogenic agent selected from *Pseudomonas* spp., *Escherichia* spp., *Staphylococcus* spp, *Candida* spp, and *Malassezia* spp.

As can be seen in the following examples, the composition according to the invention showed a surprising synergistic efficacy against said pathogenic agents, due to the association of lactoferricin and lactoferrampin as described above.

In a still further aspect, the present invention relates to the use of said composition as a prebiotic agent in products for human or animal feeding. Indeed, it has been unexpectedly found that, not only is the composition according to the invention synergistically effective against the pathogenic agents stated above, but also has a higher prebiotic index than that obtained for prebiotics commonly used, namely FOS (fructo-oligosaccharides) and GOS (galacto-oligosaccharides). Indeed, the composition results in the growth of beneficial probiotic bacteria (including *E. faecium, L. plantarum, L. rhamnosus*) and the metabolic activities thereof and, at the same time, a reduction in the putrefactive or potentially pathogenic micro-organisms such as those stated above.

The prebiotic index was calculated by using the following formula:

$$\frac{\text{probiotic growth with respect to prebiotic } \log\frac{CFU}{\text{mL}}(24\text{ h}) - \text{probiotic growth with respect to prebiotic } \log CFU/\text{mL}(0\text{ h})}{\text{probiotic growth with respect to glucose } \log\frac{CFU}{\text{mL}}(24\text{ h}) - \text{probiotic growth with respect to glucose } \log CFU/\text{mL}(0\text{ h})} -$$

$$\frac{\text{enteric growth with respect to prebiotic } \log\frac{CFU}{\text{mL}}(24\text{ h}) - \text{enteric growth with respect to prebiotic } \log CFU/\text{mL}(0\text{ h})}{\text{enteric growth with respect to glucose } \log\frac{CFU}{\text{mL}}(24\text{ h}) - \text{enteric growth with respect to glucose } \log CFU/\text{mL}(0\text{ h})}$$

As a result, the higher the index, the greater the prebiotic character of the compound tested.

In the following examples, the prebiotic character of the composition according to the invention is shown in comparison with that of FOS.

The present invention relates to a food or feed product comprising the composition described herein and suitable food-grade ingredients.

In a still further aspect, the present invention relates to formulations comprising said composition and at least one plant extract.

Preferred plant extracts are extracts of bearberry, green tea, cranberry, blueberry, *eucalyptus*, witch hazel, soya, and mixtures thereof.

It has surprisingly been observed that the composition according to the invention, when mixed with at least one plant extract, shows a further synergistic effect.

In a still further aspect, the present invention relates to formulations comprising said composition and at least one other natural antimicrobial peptide.

Said natural antimicrobial peptide is preferably nisin, beta defensin, LL-37, temporin A, temporin B, temporin L, indolicidin, melittin, protegrin-1, protegrin-2, protegrin-3, protegrin-4, protegrin-5, magainin 2, RTD-1, RTD-2, RTD-3, RTD-4, RTD-5, arenicin-1, arenicin-2, arenicin-3, dermcidin, cecropin, andropin, moricin, ceratotoxin, dermaseptin, bombinin, preferably maximin H1, maximin H2, maximin H3, maximin H4, or maximin H5, esculentin, ranalexin, buforin II, human CAP18, abaecin, apidaecin, profenin, bactenecin, brevinin-1, brevinin-2, tachiplesin, drosomycin, or a mixture thereof.

In preferred embodiments, said natural antimicrobial peptide is nisin.

Indeed, it has been observed that the composition according to the invention, when mixed with at least one other natural antimicrobial peptide, shows a further synergistic effect.

It should be understood that all the possible combinations of preferred aspects of the components of the composition, as above reported, are to be deemed as hereby disclosed.

It should be understood also that all the aspects identified as preferred and advantageous for the composition and its components are to be deemed as similarly preferred and advantageous also for the preparations and uses thereof.

Below are working examples of the present invention provided for illustrative purposes.

EXAMPLES

Example 1

Provided below are examples of enzymatic immobilisation procedures which can be performed in order to obtain biocatalysts to be used in the production of lactoferrin hydrolysate comprising the composition of interest.

a) Enzyme Immobilisation #1 (Hydrochloric Acid)

Prepare an aqueous solution of HCl with a concentration of 10 mM.

Add powdered pork pepsin with a concentration of 25 mg/mL and leave under stirring until completely dissolved.

Measure the pH and adjust to 2.00±0.20 by using an aqueous solution of hydrochloric acid or sodium hydroxide.

Add epoxy resin, with a concentration of 250 mg/mL, to the enzymatic suspension and leave under stirring for 4 h.

Remove the unbound enzyme solution by means of at least 3 washes with an equal volume of the HCl 10 mM+NaCl 1 M solution.

After the last wash, use a vacuum pump to remove the liquid fraction from the enzyme immobilised on resin, and then store the resin at 4° C.

Titrate the enzymatic activity by using the standard protocol (Yoshida, F. (1956), Bull. Agri. Chem. Soc Japan 20, 252-256) with 2% (w/v) haemoglobin as the substrate.

b) Enzyme Immobilisation #2 (Phosphoric Acid)

Prepare an aqueous solution of 85% (w/w) phosphoric acid with a concentration of 1.25% (v/v).

Add powdered pork pepsin with a concentration of 25 mg/mL and leave under stirring until completely dissolved.

Measure the pH and adjust to 2.00±0.20 by using an aqueous solution of phosphoric acid or potassium hydroxide.

Add epoxy resin, with a concentration of 250 mg/mL, to the enzymatic suspension and leave under stirring for 4 h.

Remove the unbound enzyme solution by means of at least 3 washes with an equal volume of the aqueous solution of 1.25% (v/v) phosphoric acid+NaCl 1 M.

After the last wash, use a vacuum pump to remove the liquid fraction from the enzyme immobilised on resin, and then store the resin at 4° C.

Titrate the enzymatic activity using the standard protocol (Yoshida, F. (1956), Bull. Agri. Chem. Soc Japan 20, 252-256) with 2% (w/v) haemoglobin as the substrate.

Example 2

Lactoferrin Hydrolysis Process by Using Immobilised Enzyme #1 (HCl/glycine)

Prepare an aqueous solution of glycine with a concentration of 3 g/L.

Keep the solution under stirring and slowly add lactoferrin powder to a concentration of 130 g/L and wait until it is completely dissolved.

Adjust the pH of the suspension to 2.1±0.10 by using an aqueous solution of hydrochloric acid.

Add immobilised pepsin to a concentration of 32.5 to 65 U/mL (measured by titration on a standard 2% (w/w) haemoglobin substrate.)

Within 2 hours of reaction at a temperature of 20-30° C., the immobilised enzyme is removed using calibrated sieves which efficiently separate the liquid fraction (hydrolysate of lactoferrin) from the solid fraction (spent immobilised enzyme).

Analyse the hydrolysis profile of the product by HPLC and measure the presence of lactoferricin.

Example 3

Lactoferrin Hydrolysis Process by Using Immobilised Enzyme #2 (Phosphoric Acid)

Prepare an aqueous solution of lactoferrin with a concentration of 130 g/L, keep the solution under stirring and wait until the complete dissolution thereof.

Adjust the pH of the suspension to 2.1±0.10 using a solution of 85% (w/v) phosphoric acid.

Add immobilised pepsin to a concentration of 65 to 130 U/mL (measured by titration on a standard 2% (w/w) haemoglobin substrate).

Within 2 hours of reaction at a temperature of 20-30° C., the immobilised enzyme is removed by using calibrated sieves which efficiently separate the liquid fraction (hydrolysate of lactoferrin) from the solid fraction (spent immobilised enzyme).

Analyse the hydrolysis profile of the product by HPLC and measure the presence of lactoferricin.

Example 4

Lactoferrin Hydrolysis Process by Using Immobilised Enzyme #3 (Lactic Acid/Phosphoric Acid) Prepare an aqueous solution of 80% (w/w) lactic acid with a concentration of 2% (v/v).

Keep the solution under stirring and slowly add lactoferrin powder until a concentration of 130 g/L and wait until it is completely dissolved.

Adjust the pH of the suspension to 2.1±0.10 by using an aqueous solution of 85% (w/v) phosphoric acid.

Add immobilised pepsin to a concentration of 65 to 130 U/mL (measured by titration on a standard 2% (w/w) haemoglobin substrate.)

Within 2 hours of reaction at a temperature of 20-30° C., the immobilised enzyme is removed by using calibrated sieves which efficiently separate the liquid fraction (hydrolysate of lactoferrin) from the solid fraction (spent immobilised enzyme).

Analyse the hydrolysis profile of the product by HPLC and measure the presence of lactoferricin.

Example 5

Lactoferrin Hydrolysis Process by Using Immobilised Enzyme #4 (Lactic Acid)

Prepare an aqueous solution of lactoferrin with a concentration of 130 g/L, keep the solution under stirring and wait until the complete dissolution thereof.

Add 80% (w/w) lactic acid to an end concentration of 2% (v/v).

Add immobilised pepsin to a concentration of 32.5 to 65 U/mL (measured by titration on a standard 2% (w/w) haemoglobin substrate).

After 2 hours of reaction at a temperature of 20-30° C., the immobilised enzyme is removed using calibrated sieves which efficiently separate the liquid fraction (hydrolysate of lactoferrin) from the solid fraction (spent immobilised enzyme).

Analyse the hydrolysis profile of the product by HPLC and measure the presence of lactoferricin.

Example 6

Lactoferrin Hydrolysis Process by Using Immobilised Enzyme #4 (for the Production of Lactoferrampin)

Prepare an aqueous solution of lactoferrin with a concentration of 130 g/L, keep the solution under stirring and wait until the complete dissolution thereof.

Buffer the solution to a pH of 7.0 to 9.0 using a tris-Cl or ammonium bicarbonate buffer with a concentration of 10 mM to 100 mM.

Add the following pairs of free or immobilised enzymes with a concentration of 0.01% to 10% (w/v):

- clostripain and XVII-type protease (endoproteinase GLU-C);
- clostripain and endoprotease ASP-N;
- endoproteinase ARG-C and XVII-type protease (endoproteinase GLU-C)
- endoproteinase ARG-C and endoprotease ASP-N.

Before use, the clostripain enzyme requires a 4 h activation phase in the presence of 2.5 mM DTT and 1 mM CaCl2.

Incubate the reaction at a temperature of 25 to 37° C., monitoring the production of lactoferrampin by HPLC. Once hydrolysis is complete, inhibit the reaction by removing the immobilised enzyme (in the case of biocatalysts on solid substrates) or by reducing the pH to 4.00 by means of 3M HCl (in the case of a free enzyme).

Example 7

The antimicrobial activity of the composition according to the invention has been assessed in relation to gram-positive and gram-negative bacteria, as well as fungi and yeast, by means of in vitro susceptibility testing with the antimicrobial dilution method (CLSI protocols—Clinical and Laboratory Standards Institute), as a result of which the MIC (Minimum Inhibitory Concentration) was determined for each of the microorganisms in question.

For all the tests carried out, a positive control for the antimicrobial activity was carried out by using fluconazole (for fungi and yeasts) and ceftriaxone (for bacterial strains) and a negative control (no compounds) in which the correct microbial growth was assessed.

First, the individual antimicrobial activity of the two peptides (lactoferricin and lactoferrampin) was determined:

Activity (MIC) against *S. intermedius* ATCC 29663

| | Lactoferricin (μg/mL) | Lactoferrampin (μg/mL) |
|---|---|---|
| *S. intermedius* | 6.25 | 200 |

Activity (MIC) against *M. pachydermatis* DSM 6172

| | Lactoferricin (μg/mL) | Lactoferrampin (μg/mL) |
|---|---|---|
| *M. pachydermatis* | 6.25 | 200 |

The antimicrobial activity of the combined (two) peptides was then determined:

| | $FIC_{index}$(lactoferricin + lactoferrampin) |
|---|---|
| *S. intermedius* | 0.5 |
| *M. pachydermatis* | 0.5 |

The FIC index is determined using the following formula:

$$FIC\ \text{index} = \frac{MIC\ \text{of}\ A\ \text{in combination with}\ B}{MIC\ \text{of}\ A\ \text{alone}} + \frac{MIC\ \text{of}\ B\ \text{in combination with}\ A}{MIC\ \text{of}\ B\ \text{alone}}$$

where A is lactoferricin and B is lactoferrampin

FIC index <1=> demonstrated a synergistic effect, i.e. the activity of the two components together is greater than the sum of their activities when measured separately.

FIC Index>1=> no synergistic effect

From the experimental data obtained and shown in the table above, the synergistic action of the combined (two) peptides is clear.

Example 8

A composition according to the present invention was prepared, wherein lactoferricin and lactoferrampin are in a weight ratio of 1:1.5, by mixing the lactoferrin hydrolysate containing lactoferricin obtained in Example 2 and the lactoferrin hydrolysate containing lactoferrampin obtained in Example 6.

Example 9

The composition in Example 8 and a product comprising fructooligosaccharides (FOS, Fructooligosaccharides from chicory, marketed by Sigma Aldrich) were brought into contact (with different concentrations) with the probiotic micro-organisms or pathogens. After 24 hours of incubation, the bacterial count in terms of CFU/ml (plating on optimal agar medium) was assessed to evaluate growth; this parameter was compared with growth in the presence of glucose.

The formula used to obtain the prebiotic index is as follows:

$$\frac{\text{probiotic growth with respect to prebiotic}\ \log\frac{CFU}{\text{mL}}(24\ \text{h}) - \text{probiotic growth with respect to prebiotic}\ \log\ CFU/\text{mL}(0\ \text{h})}{\text{probiotic growth with respect to glucose}\ \log\frac{CFU}{\text{mL}}(24\ \text{h}) - \text{probiotic growth with respect to glucose}\ \log\ CFU/\text{mL}(0\ \text{h})} -$$

$$\frac{\text{enteric growth with respect to prebiotic}\ \log\frac{CFU}{\text{mL}}(24\ \text{h}) - \text{enteric growth with respect to prebiotic}\ \log\ CFU/\text{mL}(0\ \text{h})}{\text{enteric growth with respect to glucose}\ \log\frac{CFU}{\text{mL}}(24\ \text{h}) - \text{enteric growth with respect to glucose}\ \log\ CFU/\text{mL}(0\ \text{h})}$$

Below are the prebiotic indices at specific concentrations of FOS and the composition in Example 8.

As stated in the description, the higher the index, the greater the prebiotic character of the compound tested.

Growth of *E. faecium* (vs. *S. interditis*)

| | Prebiotic Index | |
|---|---|---|
| Concentration (mg/ml) | FOS | Composition in Example 8 |
| 20 | 0.122 | 1.040 |
| 15 | 0.128 | 1.041 |
| 10 | 0.155 | 0.602 |
| 5 | 0.232 | 0.361 |
| 1 | 0.355 | 0.317 |
| 0.5 | 0.316 | 0.279 |
| 0.1 | 0.441 | 0.295 |

Growth of *L. plantarum* (vs. *S. interditis*)

| | Prebiotic Index | |
|---|---|---|
| Concentration (mg/ml) | FOS | Composition in Example 8 |
| 20 | 0.119 | 1.099 |
| 15 | 0.132 | 1.095 |
| 10 | 0.160 | 0.662 |
| 5 | 0.244 | 0.401 |
| 1 | 0.386 | 0.342 |
| 0.5 | 0.353 | 0.303 |
| 0.1 | 0.478 | 0.314 |

Growth of *L. rhamnosus* (vs. *S. interditis*)

| | Prebiotic Index | |
|---|---|---|
| Concentration (mg/ml) | FOS | Composition in Example 8 |
| 20 | 0.148 | 0.592 |
| 15 | 0.168 | 0.977 |
| 10 | 0.188 | 0.594 |
| 5 | 0.268 | 0.361 |
| 1 | 0.394 | 0.322 |
| 0.5 | 0.362 | 0.294 |
| 0.1 | 0.483 | 0.310 |

The data above clearly shows the prebiotic character of the composition according to the invention.

Example 10

In this example, the antimicrobial activity of the individual natural extracts was first assessed as follows:

| MIC (mg/ml) Bearberry | | | | |
|---|---|---|---|---|
| *S. aureus* | *S. epidermidis* | *P. larvae* | *P. gingivalis* | *C. albicans* |
| 6.25 | 3.125 | 0.78 | 0.384 | 0.39 |

| MIC (mg/ml) Cranberry | | | |
|---|---|---|---|
| *S. aureus* | *E. coli* | *P. aeruginosa* | *C. albicans* |
| 0.78 | 3.125 | 0.78 | 1.56 |

| MIC (mg/ml) Blueberry | | |
|---|---|---|
| *E. coli* | *P. aeruginosa* | *C. albicans* |
| 1.56 | 12.5 | 6.25 |

-continued

| | Micro-organism - MIC (mg/ml) |
|---|---|
| Green tea | *E. coli* - 22.5 mg/ml |
| Eucalyptus | *C. albicans* 3.125 mg/ml |
| Witch hazel | *C. albicans* 12.5 mg/ml |
| Soya | *P. acnes* - 0.195 mg/ml |

The antimicrobial activity of the individual natural extracts was then assessed in association with the composition according to the invention in Example 8:

| | Extract mixed with Example 8 | $FIC_{index}$ |
|---|---|---|
| *P. larvae* | Bearberry | 0.2 |
| *E. coli* | Green tea | 0.65 |
| *S. epidermidis* | Bearberry | 0.4 |
| *C. albicans* | Bearberry | 0.2 |
| *C. albicans* | Cranberry | 0.3 |
| *C. albicans* | Blueberry | 0.28 |
| *C. albicans* | Eucalyptus | 0.15 |
| *C. albicans* | Witch hazel | 0.1 |
| *S. aureus* | Bearberry | 0.5 |
| *S. aureus* | Cranberry | 0.75 |
| *P. acnes* | Soya | 0.75 |
| *P. gingivalis* | Bearberry | 0.2 |

Also in this case, a further, unexpected synergistic effect was observed between the composition according to the invention and the plant extracts.

Example 11

The interaction of the composition in Example 8 with other natural antimicrobial peptides, such as nisin, was assessed.

The data obtained shows that the two compounds establish a synergistic interaction with each other, as stated below:

| | Micro-organism - MIC (UI/ml) | |
|---|---|---|
| Nisin | *E. coli* - 18750 UI/ml | *S. aureus* - 17 UI/ml |

After determining the antimicrobial activity of nisin alone, the antimicrobial activity of nisin was assessed in association with the composition according to the invention:

| | $FIC_{index}$(Nisin + Example 8) |
|---|---|
| *E. coli* | 0.15 |
| *S. aureus* | 0.37 |

Also in this case, a further, unexpected synergistic effect was observed between the composition according to the invention and the natural antimicrobial peptides.

The invention claimed is:

1. A method for the treatment of infections caused by *Malassezia pachydermatic* or *B subtilis*, said method comprising administering to a subject in need thereof a composition comprising an effective amount of lactoferricin and an effective amount of lactoferrampin, wherein lactoferricin is in a molar amount lower than lactoferrampin, wherein lactoferricin and lactoferrampin are in a weight ratio of at least 1:1.5, and wherein the molar ratio of lactoferricin and lactoferrampin is from 1:2.5 to 1:81.

2. The method according to claim 1, wherein lactoferricin and lactoferrampin are in a weight ratio not higher than 1:100.

3. The method according to claim 1, wherein lactoferricin and lactoferrampin are in a weight ratio of 1:2 to 1:50.

4. The method according to claim 1, wherein the composition comprises 0.01 wt % to 1 wt % of lactoferricin and 0.02 wt % to 10 wt % of lactoferrampin, based on the composition weight.

5. The method according to claim 1, wherein lactoferricin or lactoferrampin is obtained by enzymatic hydrolysis of lactoferrin.

6. The method according to claim 5, wherein said enzymatic hydrolysis occurs through an immobilized enzyme.

* * * * *